US 6,708,688 B1

(12) United States Patent
Rubin et al.

(10) Patent No.: US 6,708,688 B1
(45) Date of Patent: Mar. 23, 2004

(54) METERED DOSAGE INHALER SYSTEM WITH VARIABLE POSITIVE PRESSURE SETTINGS

(76) Inventors: Darren Rubin, 3844 Chaucer Way, Land O'Lakes, FL (US) 34639;
Howard Rubin, 3844 Chaucer Way, Land O'Lakes, FL (US) 34639

( * ) Notice: Subject to any disclaimer, the term of this patent is extended or adjusted under 35 U.S.C. 154(b) by 247 days.

(21) Appl. No.: 10/014,618

(22) Filed: Dec. 11, 2001

(51) Int. Cl.⁷ .............................................. A61M 11/00
(52) U.S. Cl. ........................ 128/200.23; 128/200.24; 128/203.23; 128/205.23; 600/529; 482/13
(58) Field of Search ........................... 600/529–543; 128/200.14–200.24, 202.13, 203.12, 203.15, 204.18, 203.23, 205.23, 207.14–207.18; 482/13

(56) References Cited

U.S. PATENT DOCUMENTS

| | | | | |
|---|---|---|---|---|
| 3,898,987 A | * | 8/1975 | Elam | 600/532 |
| 4,198,969 A | * | 4/1980 | Virag | 128/200.21 |
| 4,444,202 A | * | 4/1984 | Rubin et al. | 128/200.23 |
| 5,522,380 A | * | 6/1996 | Dwork | 128/200.23 |

\* cited by examiner

*Primary Examiner*—Glenn K. Dawson
(74) *Attorney, Agent, or Firm*—Edward P. Dutkiewicz

(57) ABSTRACT

A metered dosage inhaler system with variable positive pressure settings has a hollow housing with a front portion with a cylindrical protruding user adaptor portion, a top face having apertures, a user controlled air resistance dial, a bottom face having a handle/input, and a cylindrical downwardly extending hollow handle portion. The first end of the handle portion is adapted to form an airtight removable coupling with the handle/input adaptor. An end piece with holes is adapted to couple to the second end of the handle portion. A spherical ball has a diameter less than that of the handle portion and removably rests in the handle portion. The ball rises in response to a vacuum caused by a,patient. A mouth piece portion has a cylindrical first portion removably coupled to the adapter portion and a tapered second portion adapted to fit comfortably within the mouth of a patient.

7 Claims, 5 Drawing Sheets

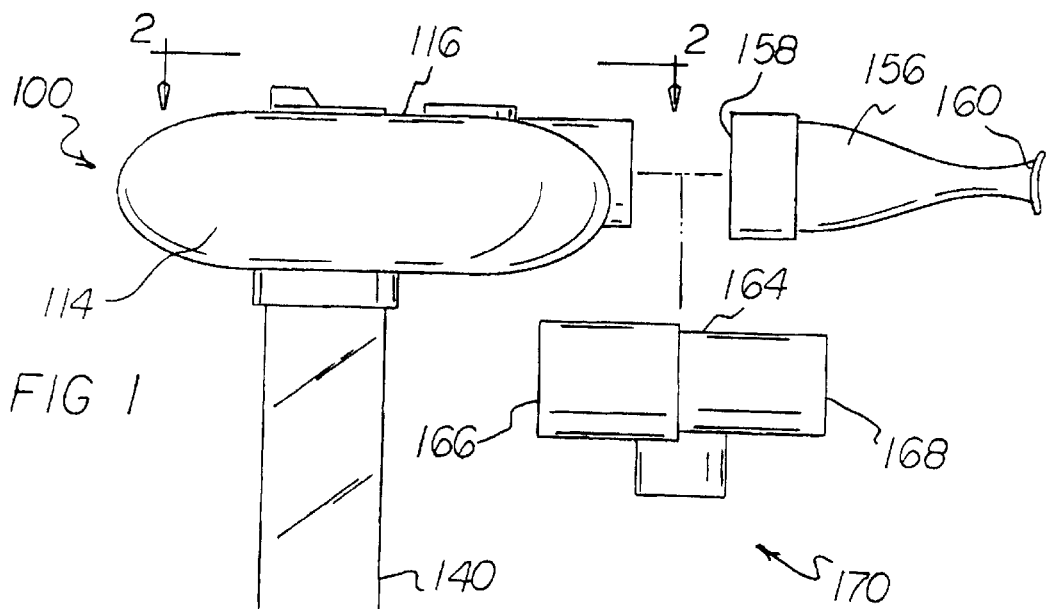
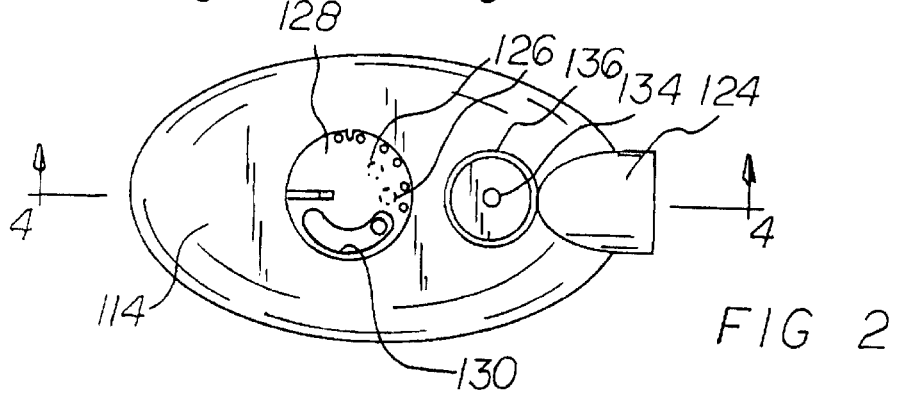
FIG 1
FIG 2

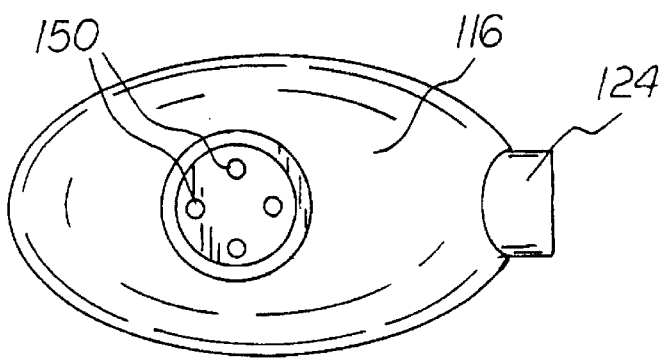
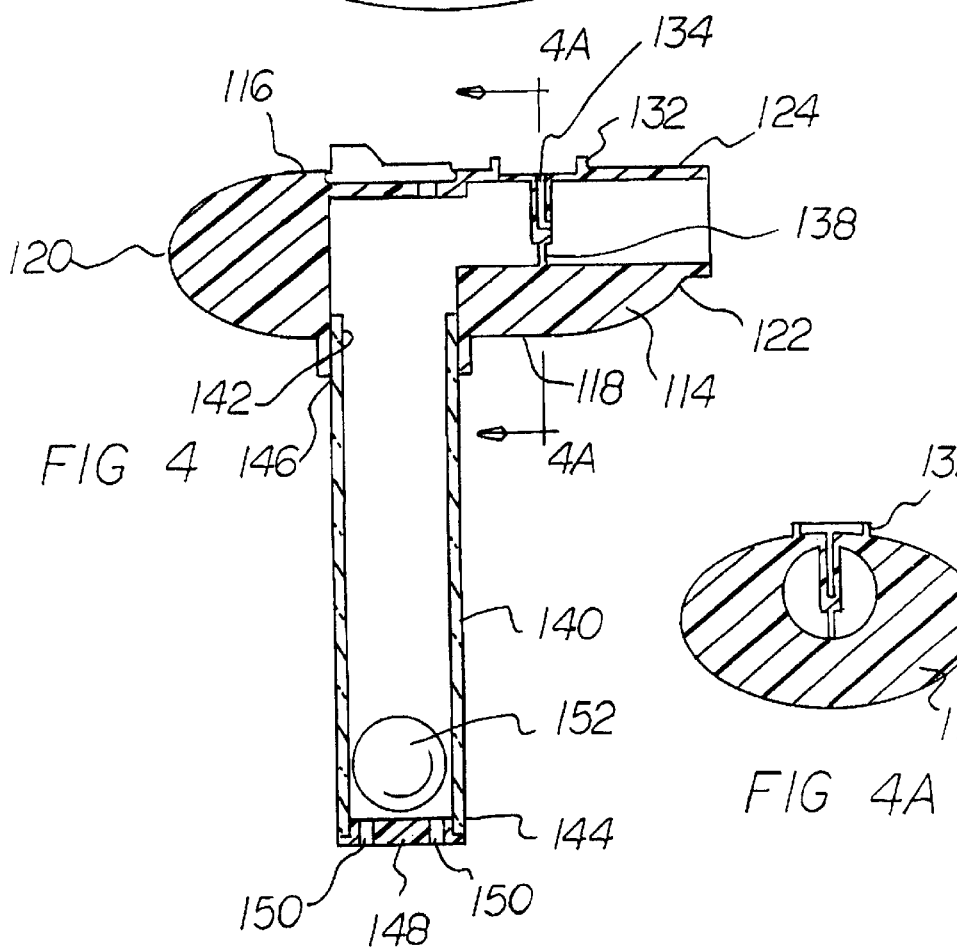

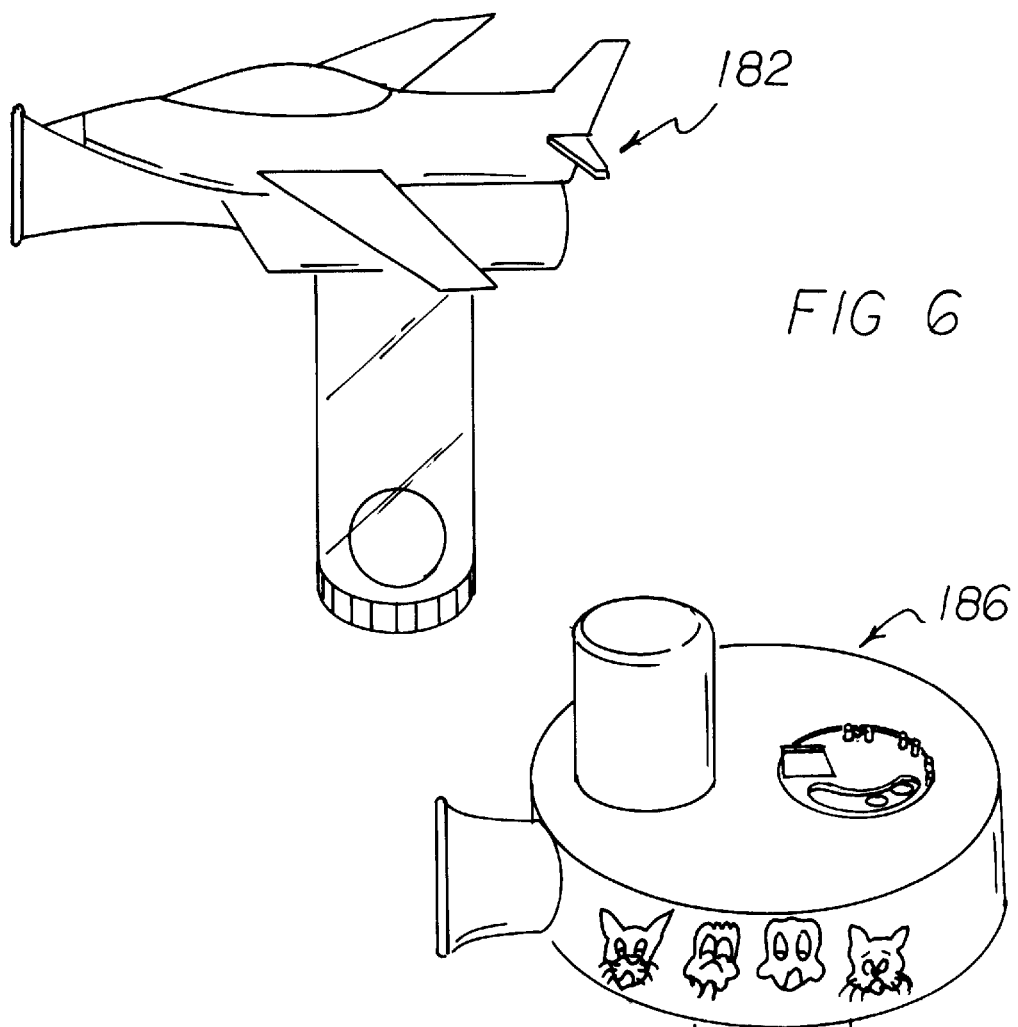

METERED DOSAGE INHALER SYSTEM WITH VARIABLE POSITIVE PRESSURE SETTINGS

BACKGROUND OF THE INVENTION

1. Field of the Invention

The present invention relates to a metered dosage inhaler system with variable positive pressure settings and more particularly pertains to providing inhaled medication and exercise to the lungs of a patient.

2. Description of the Prior Art

The use of inhalers of known designs and configurations is known in the prior art. More specifically, inhalers of known designs and configurations previously devised and utilized for the purpose of providing medication and/or exercise to the lungs of a user through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,040,527 to Larson, et al discloses a metered dose inhalation unit with slide means. U.S. Pat. No. 6,039,042 to Sladek discloses a portable chamber for meter dose inhaler dispenser. U.S. Pat. No. 5,522,380 to Dwork discloses a metered dose medication adaptor with improved incentive spirometer. U.S. Pat. No. 5,899,832 to Hougen discloses a compact lung exercising device. U.S. Pat. No. 4,207,884 to Isaacson discloses a pressure controlled breathing apparatus. U.S. Pat. No. 4,259,952 to Chernack et al. discloses a dual valve for respiratory device. Lastly, U.S. Pat. No. 4,444,202 to Rubin discloses a breathing excersiser.

While these devices fulfill their respective, particular objectives and requirements, the aforementioned patents do not describe a metered dosage inhaler system with variable positive pressure settings that allows providing inhaled medication and exercise to the lungs of a patient.

In this respect, the metered dosage inhaler system with variable positive pressure settings according to the present invention substantially departs from the conventional concepts and designs of the prior art, and in doing so provides an apparatus primarily developed for the purpose of providing inhaled medication and exercise to the lungs of a patient.

Therefore, it can be appreciated that there exists a continuing need for a new and improved metered dosage inhaler system with variable positive pressure settings which can be used for providing inhaled medication and exercise to the lungs of a patient. In this regard, the present invention substantially fulfills this need.

SUMMARY OF THE INVENTION

In view of the foregoing disadvantages inherent in the known types of inhalers of known designs and configurations now present in the prior art, the present invention provides an improved metered dosage inhaler system with variable positive pressure settings. As such, the general purpose of the present invention, which will be described subsequently in greater detail, is to provide a new and improved metered dosage inhaler system with variable positive pressure settings and method which has all the advantages of the prior art and none of the disadvantages.

To attain this, the present invention essentially comprises a one piece housing. The one piece housing has an oblong configuration with a generally planar top face and bottom face. The housing also has a rounded rear face and a generally rounded front portion. The front portion has a cylindrical protruding user adaptor portion. The top face has apertures and a user controlled air resistance dial with supplemental apertures. The user controlled air resistance is parallel with the top face and rotatable for controlling the amount of additional air allowed to enter through apertures associated with the dial. The top face further includes a flush circular medication adaptor. The medication adaptor has a small aperture passing there through with a circular lip extending outwardly for supporting a container within the small aperture. The bottom face has a handle/input adaptor comprised of a cylindrical extension pointing downward and lying in a common axis with the resistance dial. The hollow interior couples the handle adaptor aperture with the aperture of the user adaptor portion. Next provided is a downwardly extending handle portion. The handle portion is of a cylindrical configuration. The handle portion has a first end and a second end. The first end is adapted to form an airtight removable coupling with the handle/input adaptor of the housing. An end piece is next provided. The end piece has holes adapted to couple to the second end of the handle portion to define an interior space and allow air passage through the system. Next, a spherical ball is provided. The spherical ball has a diameter less than that of the handle portion. The spherical ball is adapted to removably rest in the handle portion and form a resistance to the air flow through the holes of the end piece thus contributing to the resistant flow of air through the housing. The ball is adapted to rise in response to a vacuum caused by a patient during use. A mouth piece portion is next provided. The mouth piece portion has a cylindrical first portion adapted to removably couple with respect to the adapter portion. The mouth piece also has a tapered second portion. The second portion is adapted to fit comfortably within the mouth of a patient. Next provided is an optional extension portion of a generally hollow cylindrical configuration. The extension portion has a body, a primary end and a secondary end. The primary end is adapted to removably couple with the user adaptor portion and the secondary end is adapted to couple with the first portion of the mouth piece. The body has a downward facing aperture with a neck. Lastly, an additional optional extension portion is provided. The additional extension portion has a downwardly facing aperture. A supplemental medication container is adapted to couple with the downwardly facing aperture to a patient.

There has thus been outlined, rather broadly, the more important features of the invention in order that the detailed description thereof that follows may be better understood and in order that the present contribution to the art may be better appreciated. There are, of course, additional features of the invention that will;be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved metered dosage inhaler system with variable positive pressure settings which has all of the advantages of the prior art inhalers of known designs and configurations and none of the disadvantages.

It is another object of the present invention to provide a new and improved metered dosage inhaler system with variable positive pressure settings which may be easily and efficiently manufactured and marketed.

It is further object of the present invention to provide a new and improved metered dosage inhaler system with variable positive pressure settings which is of durable and reliable constructions.

An even further object of the present invention is to provide a new and improved metered dosage inhaler system with variable positive pressure settings which is susceptible of a low cost of manufacture with regard to both materials and labor, and which accordingly is then susceptible of low prices of sale to the consuming public, thereby making such metered dosage inhaler system with variable positive pressure settings economically available to the buying public.

Even still another object of the present invention is to provide a metered dosage inhaler system with variable positive pressure settings for providing inhaled medication and exercise to the lungs of a patient.

Lastly, it is an object of the present invention to provide a new and improved metered dosage inhaler system with variable positive pressure settings having a hollow housing. The housing has a front portion with a cylindrical protruding user adaptor portion, a top face having apertures and a user controlled air resistance dial, and a bottom face having a handle/input. A cylindrical downwardly extending hollow handle portion has a first end and a second end. The first end is adapted to form an airtight removable coupling with the handle/input adaptor. An end piece with holes is adapted to couple to the second end of the handle portion. A spherical ball has a diameter less than that of the handle portion and is adapted to removably rest in the handle portion. The ball is adapted to rise in response to a vacuum caused by a patient during use. A mouth piece portion has a cylindrical first portion adapted to removably couple with respect to the adapter portion and a tapered second portion adapted to fit comfortably within the mouth of a patient.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an exploded side elevational illustration of the present invention.

FIG. 2 is a top elevational view of the housing built in accordance with the principles of the present invention taken along line 3—3 of FIG. 1.

FIG. 3 is a rear elevational view of the housing built in accordance with the principles of the present invention.

FIG. 4 is a cross sectional view of the housing and handle portion taken along line 4—4 of FIG. 2.

FIG. 4A is a cross sectional view taken along line 4A—4A of FIG. 3.

FIG. 6 in a perspective illustration of an alternative embodiments of the present invention wherein the housing takes on the shapes of an airplane.

FIG. 7 in a perspective illustration of an alternative embodiments of the present invention wherein the housing has various indicia.

The same reference numerals refer to the same parts throughout the various Figures.

DESCRIPTION OF THE PREFERRED EMBODIMENT

Figure 5:
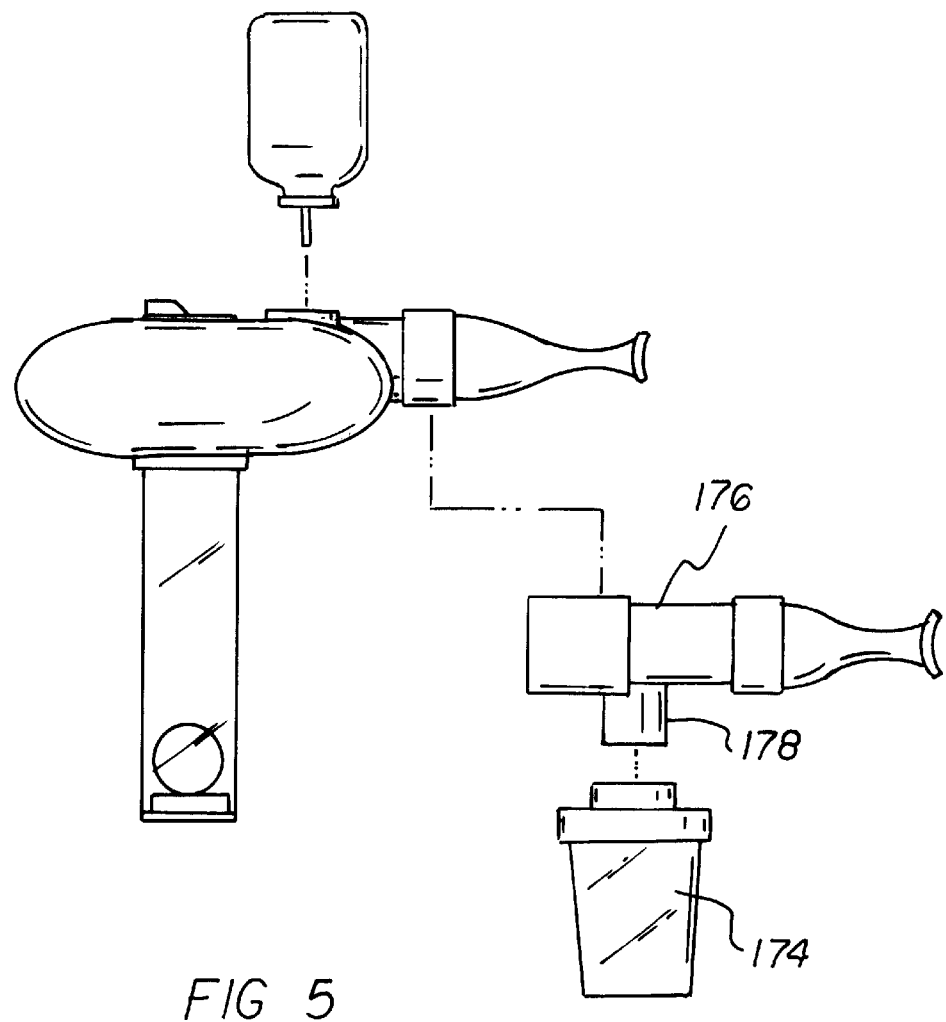
FIG. 5 is an exploded view of an alternative embodiment of the present invention including an extension portion.

With reference now to the drawings, and in particular to FIG. 1 thereof, the preferred embodiment of the new and improved metered dosage inhaler system with variable positive pressure settings embodying the principles and concepts of the present invention and generally designated by the reference numeral 100 will be described.

The present invention, the metered dosage inhaler system with variable positive pressure settings 100 is comprised of a plurality of components. Such components in their broadest context include a handle, an end piece, a ball and a mouthpiece. Such components are individually configured and correlated with respect to each other so as to attain the desired objective.

Figure 8:
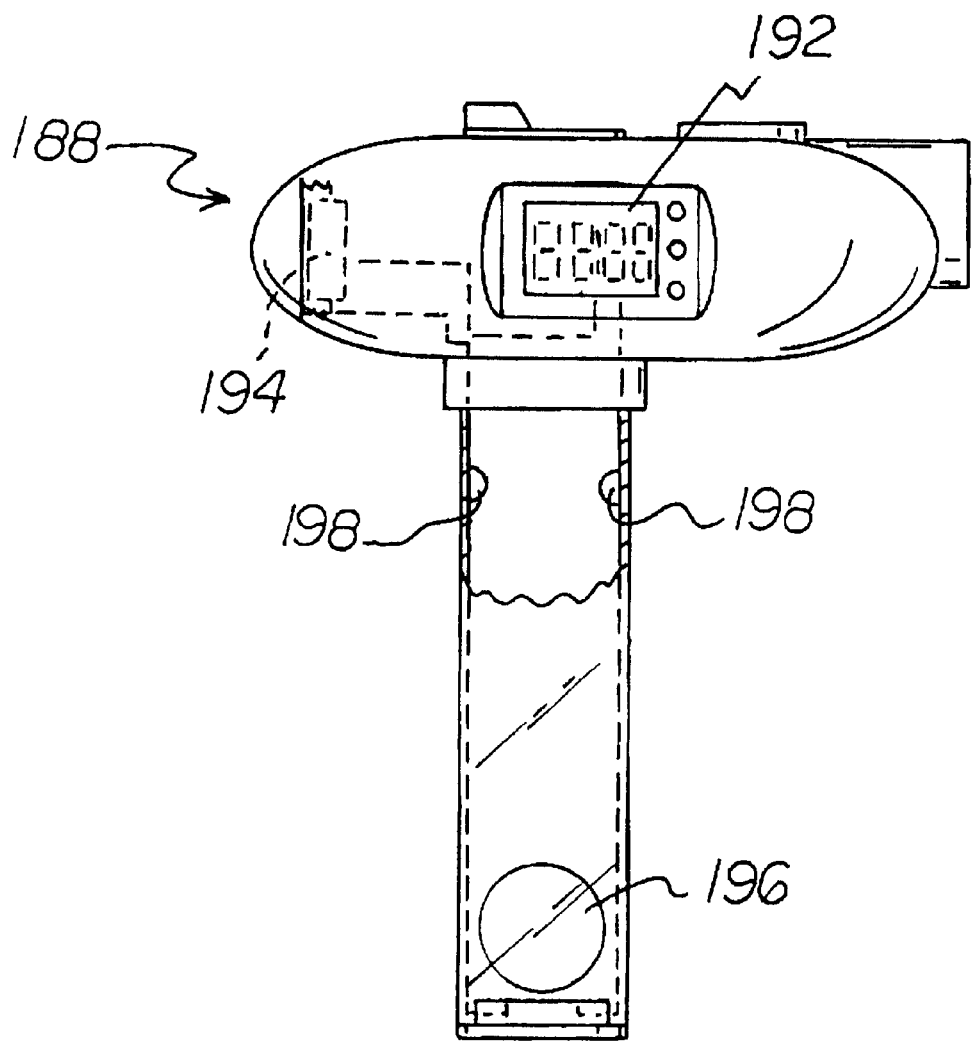
FIG. 8 is a side elevational view of the final embodiment of the invention.

Various embodiments of the invention are illustrated in FIGS. 1 through 8. In the primary embodiment of FIGS. 1 through 5, a metered dosage inhaler system 100 with variable positive pressure settings for providing medication and exercise to the lungs of a patent is shown. First provided in this embodiment is a one piece housing 114. The one piece housing has an oblong configuration with a generally planar top face 116 and bottom face 118. The housing also has a rounded rear face 120 and a generally rounded front portion 122. The front portion has a cylindrical protruding user adaptor portion 124. The top face has apertures 126 and a user controlled air resistance dial 128 with supplemental apertures 130. The user controlled air resistance is parallel with the top face and rotatable for controlling the amount of additional air allowed to enter through apertures associated with the dial. The top face further includes a flush circular medication adaptor 132. The medication adaptor has a small aperture 134 passing there through with a circular lip 136 extending outwardly for supporting a container within the small aperture. The bottom face has a handle/input adaptor comprised of a cylindrical extension pointing downward and lying in a common axis with the resistance dial. The hollow interior couples the handle adaptor aperture with the aperture of the user adaptor portion.

Next provided is a downwardly extending handle portion 140. The handle portion is of a cylindrical configuration. The handle portion has a first end 142 and a second end 144. The first end is adapted to form an airtight removable coupling 146 with the handle/input adaptor of the housing.

An end piece 148 is next provided. The end piece has holes 150 adapted to couple to the second end of the handle portion to define an interior space and allow air passage through the system.

Next, a spherical ball 152 is provided. The spherical ball has a diameter less than that of the handle portion. The spherical ball is adapted to removably rest in the handle portion and form a resistance to the air flow through the holes of the end piece thus contributing to the resistant flow of air through the housing. The ball is adapted to rise in response to a vacuum caused by a patient during use.

A mouth piece portion 156 is next provided. The mouth piece portion has a cylindrical first portion 158 adapted to removably couple with respect to the adapter portion. The mouth piece also has a tapered second portion 160. The second portion is adapted to fit comfortably within the mouth of a patient.

Next provided is an optional extension portion 164 of a generally hollow cylindrical configuration. The extension portion has a body, a primary end 166 and a secondary end 168. The primary end is adapted to removably couple with the user adaptor portion and the secondary end is adapted to couple with the first portion of the mouth piece. The body has a downward facing aperture 170 with a neck.

Lastly, an additional optional extension portion 172 is provided. The additional extension portion has a downwardly facing aperture 174. A supplemental medication container is adapted to couple with the downwardly facing aperture to a patient.

Most current metered dosage inhalers serve as plain inhalers, or inhalers with a spacer region. It is the purpose of this product to provide a metered dosage inhaler with multiple resistance settings to create strong positive pressure for medication to penetrate deeper into the lungs. It is also a purpose of this product to have an extended spacer region to serve a better reserve chamber for aerosol medication. Another purpose of this product is to deliver nebulized medications using a T-piece adapter. A further purpose is to allow this product to serve as an exerciser, when not delivering medication. A further purpose is to provide the patient with a wider range and number of resistance settings. It is also a goal to allow for easier cleansing of the product. A further goal is to allow this product to be more appealing to children. A further goal is to make the product easier to use by the elderly and sick patients. Another goal is to design a product that does not interfere with the user's field of vision. Another goal is to design a product with more efficient airflow. Calibrated resistance settings would also allow product to be used to measure a patient's inhalation lung volume, when measuring duration of inhalation. A further advantage is to store the MDI canister in or on the product when not in use or when traveling.

The proximal tube of the breathing apparatus is of extended length, compared to U.S. Pat. Nos. 4,444,202 and 5,522,380. This allows the product to serve as a better "spacer," or reserve chamber. A greater distance for the metered dosage medication to travel before reaching the user's mouth allows for the aerosolized particles to disperse more adequately. Medication released in this manner will have better suspension with smaller sized droplets. Note that particles of smaller size have a greater surface area to volume ratio allowing for better absorption by the epithelial cells lining the lungs.

The previous products mentioned have a shorter region, which hampers the particles from separating adequately. These particles have greater opportunity of colliding with each other and thus forming larger sized droplets. The problem is that less of the aerosol medication will penetrate to the deeper regions of the patient's lungs, and more of the aerosol will deposit in the patient's mouth; causing fowl tasting side affects and loss of medication.

The design of this product allows for more efficient airflow. Previous U.S. Pat. Nos. 4,444,202 and 5,522,380 utilize a spherical weight to create resistance. Air enters these products from the bottom of the base, up the main tube of greater diameter, then around the top, then down the secondary tube of lesser diameter, then curves around and travels horizontally out the proximal mouthpiece. In this manner, air must travel along four different vectors, changing directions three times. Also, the second tube may actually restrict airflow to a certain degree.

The purpose of our patent is to create a breathing device of more efficient airflow. Air enters from the base of the product, travels up the single tube to the top, then travels horizontally out the proximal mouthpiece. The "L-shaped" path has two vectors, and airflow changes direction just once.

Although the spacer region is extended in said product, the total distance air must travel upon entering the product and exiting the product, is much less than with previous designs. Said product will thus enhance the efficiency of airflow.

This product does not require the secondary tube and large plastic base of the previous inventions; U.S. Pat. Nos. 4,444,202 and 5,522,380. A product having less components would allow for a lower cost of production, and assembly; i.e. less expensive to manufacture.

Because airflow of this product travels less distance, there is less moisture accumulation than the previous inventions. This is also true because a second tube is not needed. Note that this second tube was of lesser diameter than the main tube, so that humid air would condense more. One's breath is considerably humid.

The present product does not require a secondary tube of smaller diameter, so there is less risk of bacterial contamination without this unneeded chamber. The small secondary tube serves as another chamber that could breed bacteria. Warm, moist breath can contain infectious agents, such as bacterial species Pseudomonas, and the adenovirus. The agents could adhere to the surface area of the secondary tube, thereby increasing the chance of contamination. Note that unlike the main tube of large diameter, it is much more difficult to clean the inside of the narrow secondary tube.

In addition to contamination by biological agents, dust and dirt particles can also accumulate in this secondary tube. Again, worsened by the difficulty of cleansing this narrow secondary tube.

This product is an improvement over the previous inventions for it is easier to clean, and has less number of components to take apart, cleanse, and reassemble.

U.S. Pat. No. 4,444,202 does not mention or claim its use in conjunction with a metered dosage adapter. U.S. Pat. No. 5,522,380 is a metered dosage adapter that can be used with an incentive spirometer. The problem with U.S. Pat. No. 5,522,380 is that the adapter can be easily lost, or further contaminated, when not attached to product.

It is the intention of this product to function as a metered dosage inhaler, without requiring the use of an external metered dosage adapter. Therefore, this product has a port to accept a canister of primary medication. This canister may contain a medicine, or treatment/therapy, or other types of substances. This port can accept the wide range of MDI canisters on the market. When not utilizing the MDI canister, the canister can be left in the port, or removed from the port. A cap or cover will then seal the port.

The present product may contain a cavity or compartment or clip, that can be used to store the metered dosage canister on or in the product when not in use, or when traveling. This provides a serious advantage over U.S. Pat. No. 5,522,380.

This product can accept a bottle of nebulized medication. This solution can contain a medicine, or treatment/therapy, or other types of substances. The T-shaped adapter would be placed in front of the proximal tube instead of a mouthpiece adapter, or between the end of the proximal tube and mouthpiece adapter. U.S. Pat. No 4,444,202 claims this, but Dwork's U.S. Pat. No. 5,522,380 does not mention anything about being used with a nebulizer.

Most patients currently use nebulizers with a T-piece adapter and mouthpiece. The other side of the T-piece is usually not sealed. Much medication is lost to the air this way. Said product would attach to this open side of T-piece adapter, thereby sealing it and preventing medication loss to the air. The strong positive pressure of this product would take nebulized medication deeper into the lungs than would be without said product. This enhances the effectiveness of the nebulized therapy.

It is an intention of this product to have a greater number of resistance settings, and a wider range of resistance settings than previous inventions; mainly U.S. Pat. Nos. 4,444,202 and 5,522,380. U.S. Pat. No. 5,522,380 by Dwork is limited to flow volume adjustments of 750 cc's to 3,000 cc's, with increments of 750 cc's in between.

It is the intention of said invention to provide the user with a greater selection of resistance settings. A healthy individual with moderate to good lung capacity can well exceed 3,000 cc's of resistance. For this reason, said product can provide greater resistance settings than previous inventions, for exercising the lungs. Having a greater number of intermediate resistance settings allows the patient to gradually increase resistance as their lung capacity builds with exercise and use of this product.

Also, patients with a terminal illness, such as lung cancer, can gradually decrease resistance settings as the patient's illness worsens. Therefore this product is created with a potential for a wider range of resistance settings (less than 750 cc's and beyond 3,000 cc's, and with possible increments smaller than 750 cc's).

One way to achieve this is to increase the number of holes on the venturi valve mechanism. Additional outlets would serve as exit holes where additional vacuum pressure would be lost to create greater positive pressure resistance to the lungs. However, this product is not to be limited by its design. Those skilled in the art would understand that there are numerous ways to create positive pressure resistance with this product. Other variations can include a threaded cap to open or seal up small holes. Also, other features can be added to improve product's use with the elderly, such as better grip, and easier methods to adjust resistance settings. Resistance settings could be labeled larger for those with impaired vision.

This product allows the patient to use the product without blocking the patient's field of vision. Therefore, the patient can watch television or read while utilizing this product. This behavior promotes longer and more frequent use of the product. Both previous inventions U.S. Pat. Nos. 4,444,202 and 5,522,380 have the main tube obstructing the patient's field of vision. In fact, the patient cannot see straight ahead without the product being in the way. This situation causes the patient's eyes to cross when starring at the product or looking straight ahead. This situation also may hamper the patient's use in public. Resistance settings are to be calibrated and clearly labeled. Resistance settings are measured in flow rate, which equals (volume of air) per time. When product is used in conjunction with a stopwatch, the inhalation volume of the lungs can be measured. The patient would have to breathe out fully, then time how long the patient can inhale at a particular resistance setting. Multiplying the number of seconds by the flow rate, if flow rate is in cc's per second, would give an estimate of the patient's inhalation lung capacity, or lung volume.

It is another intention to have models, or variations, of this product for younger patients. This would enhance the marketability of the product and make children more amenable to using said product. There are numerous ways to accomplish this task. Several methods are listed and not intended to be limiting.

More specifically, FIG. 6 shows an alternate embodiment of the invention. In this embodiment the housing is shaped as an airplane.

As a further alternative, FIG. 7 shows another alternate embodiment 186 of the invention. In this embodiment, the housing has indicia thereon.

Plastic components may be made of "glow-in-the-dark" materials.

Plastic moldings can be shaped into or colored with characters or other objects. One example is having the main plastic molding shaped as a jet. Another example has the product resemble a cartoon character. Other stickers or foam pieces can be place on or around said product, to create a similar effect. Product can make a desired sound with its use, such as a whistle.

A final alternate embodiment of the invention further includes a liquid crystal display panel 192 on the side of the housing. A power source in the form of a battery 194 is electrically coupled to the liquid display panel. An electrically conductive coating 196 is on the ball. Two electrically conductive contacts 198 are adapted to be seated in the ball prior to a suction being created by the user. The contacts are adapted to complete the circuit between the panel, power source and contacts when in use whereby the panel will illuminate and display in seconds the amount of time the ball is raised by the suction of the user.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A metered dosage inhaler system with variable positive pressure settings for providing medication and exercise to the lungs of a patient comprising, in combination:

a one piece housing having an oblong configuration with a generally planar top face and bottom face, a rounded rear face and a generally rounded front portion, the front portion having a cylindrical protruding user adaptor portion, the top face having apertures and a user controlled air resistance dial with supplemental apertures and parallel with the top face rotatable for controlling the amount of additional air allowed to enter through apertures associated with the dial, the top face further includes a flush circular medication adaptor, the medication adaptor having a small aperture passing therethrough with a circular lip extending outwardly for supporting a container within the small aperture, the bottom face having a handle/input adaptor comprising of a cylindrical extension pointing downward and lying in a common axis with the resistance dial, the housing having a hollow interior coupling a handle adaptor aperture with an aperture of the user adaptor portion;

a downwardly extending handle portion of a cylindrical configuration with a first end and a second end, the first end being adapted to form an airtight removably coupling with the handle/input adaptor of the housing;

an end piece with holes adapted to couple to the second end of the handle portion to define an interior space and allow air passage through the system;

a spherical ball having a diameter less than that of the handle portion and adapted to removably rest in the handle portion and forming a resistance to the air flow through the holes of the end piece thus contributing to the resistant flow of air through the housing, the ball adapted to rise and open the holes in response to a vacuum caused by a patient during use;

a mouth piece portion having a cylindrical first portion adapted to removably couple with respect to the adapter portion and a tapered second portion, the second portion adapted to fit comfortably within the mouth of a patient;

an extension portion of a generally hollow cylindrical configuration with a body, a primary end and a secondary end, the primary end adapted to removably couple with the user adaptor portion and the secondary end adapted to couple with the first portion of the mouth piece, the body having a downward facing aperture with a neck; and an additional extension portion with a downward facing aperture with a supplemental medication container adapted to couple with the downwardly facing aperture to a patient.

2. A metered dosage inhaler system with variable positive pressure settings comprising:

a hollow housing having a front portion with a cylindrical protruding user adaptor portion and a top face having apertures and a user controlled air resistance dial and a bottom face having a handle/input adaptor;

a downwardly extending hollow handle portion of a cylindrical configuration with a first end and a second end, the first end being adapted to form an airtight removable coupling with the handle/input adaptor;

an end piece with holes adapted to couple to the second end of the handle portion;

a spherical ball having a diameter less than that of the handle portion and adapted to removably rest in the handle portion, the ball adapted to rise and open the holes in response to a vacuum caused by a patient during use; and a mouth piece portion having a cylindrical first portion adapted to removably couple with respect to the adapter portion and a tapered second portion adapted to fit comfortably within the mouth of a patient.

3. The system as set forth in claim 2 and further including:

an optional extension portion of a generally hollow cylindrical configuration with a body, a primary end and a secondary end, the primary end adapted to removably couple with the user adaptor portion and the secondary end adapted to couple with the first portion of the mouth piece, the body having a downward facing aperture with a neck.

4. The system as set forth in claim 3 and further including:

an additional extension portion having a downward facing aperture with a supplemental medication container adapted to couple with the downwardly facing aperture.

5. The system as set forth in claim 2 wherein the housing is shaped as an airplane.

6. The system as set forth in claim 2 wherein the housing has indicia thereon.

7. The system as set forth in claim 2 and further including a liquid crystal display panel on the side of the housing with a power source in the form of a battery electrically coupled thereto and an electrically conductive contacts adapted to be seated on the ball prior to a suction being created by the user but adapted to complete the circuit between the panel, power source and contacts when used by a user whereby the panel will illuminate and display in seconds the amount of time the ball is raised by the suction of the user.

* * * * *